United States Patent [19]

Trail et al.

[11] Patent Number: 5,383,776
[45] Date of Patent: Jan. 24, 1995

[54] APPARATUS FOR ANALYZING POLYMER DEFECTS

[75] Inventors: George C. Trail; Jay P. Brush, both of Charlotte, N.C.

[73] Assignee: Hoechst Celanese Corporation, Somerville, N.J.

[21] Appl. No.: 999,633

[22] Filed: Dec. 31, 1992

[51] Int. Cl.⁶ .......................................... G01N 21/89
[52] U.S. Cl. ................... 425/135; 73/863.11;
    250/338.1; 250/461.1; 264/40.2; 356/239;
    356/368; 422/82.08; 425/169; 425/174.4
[58] Field of Search ............... 73/863.11, 864.81;
    356/237, 238, 430, 364, 366, 368, 367, 239;
    250/461.1, 339, 458.1, 459.1, 338.1; 425/71,
    135, 136, 137, 169, 174.4; 264/40.1, 40.2;
    436/172; 422/82.05, 82.08

[56] References Cited

U.S. PATENT DOCUMENTS

| | | | |
|---|---|---|---|
| 2,627,085 | 2/1953 | Rahm | 425/71 |
| 2,863,172 | 12/1958 | Buteux et al. | 425/71 |
| 3,557,377 | 1/1971 | Raasch | 250/219 |
| 3,659,950 | 5/1972 | Troll et al. | 356/199 |
| 3,856,414 | 12/1974 | Menary | 356/200 |
| 4,139,306 | 2/1979 | Norton | 358/106 |
| 4,152,053 | 5/1979 | Menary | 356/430 |
| 4,162,126 | 7/1979 | Nakagawa et al. | 356/237 |
| 4,184,769 | 1/1980 | Aeppli | 356/430 |
| 4,442,054 | 4/1984 | Dane et al. | 264/40.1 |
| 4,529,306 | 7/1985 | Kilham et al. | 356/237 |
| 4,605,857 | 8/1986 | Ninomiya et al. | 250/461.1 |
| 4,652,124 | 3/1987 | Bowen et al. | 356/237 |
| 4,715,717 | 12/1987 | Evans | 356/429 |
| 4,764,876 | 8/1988 | Whitener, Jr. et al. | 364/470 |
| 4,786,813 | 11/1988 | Suanberg et al. | 250/461.1 |
| 4,908,517 | 3/1990 | Imamura | 250/563 |
| 4,956,558 | 9/1990 | Batishko et al. | 250/461.1 |
| 4,982,104 | 1/1991 | Yuito | 356/430 |
| 5,001,353 | 3/1991 | Odake et al. | 250/461.1 |
| 5,037,763 | 8/1991 | Petisce | 264/40.1 |
| 5,127,726 | 7/1992 | Moran | 356/237 |
| 5,158,720 | 10/1992 | Levy | 264/40.2 |
| 5,191,393 | 3/1993 | Hignette et al. | 250/461.1 |
| 5,220,169 | 6/1993 | Ninomiya et al. | 250/461.1 |
| 5,220,178 | 6/1993 | Dreiling et al. | 236/430 |

Primary Examiner—Jay H. Woo
Assistant Examiner—Duane S. Smith
Attorney, Agent, or Firm—Philip P. McCann

[57] ABSTRACT

Apparatus for analysis of defects in polymerization reactor output, such as for gels in polyester polymer. The apparatus includes a tape forming unit, a tape analysis unit, and an image analysis computer. A sample of polymerization reactor output is converted to a tape form by compression between nip rolls and wound onto a reel. The tape reel is transferred to the tape analysis unit and the tape is threaded through an inspection zone to a takeup reel. A polyester tape is illuminated with ultraviolet light at the inspection zone and a camera captures images of gel fluorescence caused by the ultraviolet light. Interference filters are provided to attenuate background light. The signal generated by the camera is sent to an image analysis computer for determination of the total number of gels in preselected size ranges, the total area of the gels, and a defect ratio, which is defined as the total gel area divided by the area of the tape selected. Other electromagnetic radiation and sensors other than a camera may be selected for specific polymers or for specific types of defects. The data generated may be used for monitoring polymer quality and reactor performance and for scheduling of reactor maintenance.

24 Claims, 6 Drawing Sheets

APPARATUS FOR ANALYZING POLYMER DEFECTS

FIELD OF THE INVENTION

The invention claimed herein relates to methods and apparatus for detecting and analyzing defects in polymers.

BACKGROUND OF THE INVENTION

Polymers are high molecular weight chain-like structures formed by-linking together simple molecular units called monomers. Polymers are substances characterized by their viscosity, color, and softening point. Polymers are used in the manufacture of a wide variety of products, including films, foams, and textiles.

Heat and pressure are applied to monomers, typically in the presence of a catalyst in a polymerization reactor, to prepare polymers in either batch or continuous processes. Continuous processes are somewhat more typical. As a specific example, polymer from a continuous polymerization unit immediately may be supplied to a spinneret for extruding into filaments and subsequent use in various textile products. On the other hand, batch polymer typically is solidified and formed into chips, flake, or powder for subsequent processing.

Defects including gels, voids, and carbon and other solid particles in polymers can result in quality problems in products made from the polymer. Gels are a form of degraded polymer formed in polymerization reactors. Gels are thought to be areas across which the individual polymer chains are bridged and are said therefore to be "cross-linked." Gels in a polymer may cause filaments spun from the polymer to break under tension. Gels lead to brittleness and loss of tensile strength in filaments and show up as broken filaments in yarn. Also, the quality of films made from such a polymer may be compromised. Gels are believed to form in the polymerization reactors. Gels tend to form when the polymerization reactor performance has deteriorated or when a process upset has occurred.

Apparatus and methods previously have been proposed for analysis of defects in molten polymer and in polymeric films and fibers. See, for example, U.S. Pat. Nos. 4,715,717; 4,652,124; and 4,529,306. Methods and apparatus for analyzing molten polymer in a polymer reactor have the drawback that the environment is harsh for sensitive optical and electrical equipment, and can result in equipment failure and less accurate results. Films typically are analyzed after production for gels and other defects that can adversely impact the quality of the film. Analysis of defects in filaments for production of various textile products typically has been accomplished by an operator who examines a short length of spun filament under a microscope.

In particular, polyester filaments typically are examined under ultraviolet illumination. Gels that may be present in polyester polymers fluoresce in the orange/red portion of the visible spectrum of electromagnetic radiation when exposed to ultraviolet radiation. The operator counts the fluorescent gels until a predetermined count or length of filament has been reached. This method is tedious, time consuming, and allows only a minuscule fraction of the polymer to be examined. For example, evaluation of one gram of polymer can take up to 12 hours. Another drawback of this method and prior methods and apparatus for examination and analysis of products from polymer, such as films and fibers, is that a relatively large amount of product may be produced before the reactor operating conditions are corrected.

It would be desirable to provide for sampling and monitoring of a molten polymer stream with a minimum of labor to reduce the time required for inspecting the polymer and to provide for early, accurate, and reliable inspection of significant amounts of polymer. In this manner, the detection and analysis of gels in the reactor output could be used to monitor reactor performance, to indicate whether the reactor needs to be scheduled for maintenance, to provide an indication of the performance of spin pack filter systems in the case of spinning of continuous filaments, and to avoid manufacturing significant quantities of product from polymer having an unacceptable number of defects.

SUMMARY OF THE INVENTION

The invention claimed herein includes apparatus for detecting polymer defects wherein reactor output may be sampled and analyzed. Means are provided for sampling of molten polymer, transporting the polymer sample through an inspection zone, irradiating a preselected area of the polymer sample with electromagnetic radiation, and detecting and analyzing the results of the incidence of electromagnetic radiation on the sample.

Means may also be provided for performing statistical analysis, including analysis of the type and distribution of defects, to facilitate detecting out-of-spec conditions and comparing previous known data with that of the sample.

More specifically, the polymer sample is provided as a thick semi-molten monofilament from the bleed stream of a high polymerizer or a spin pack filter or may be provided from an extruder. The apparatus includes a device for converting the semi-molten monofilament into a tape having a high ratio of surface area to volume for optical inspection. A guide guides the semi-molten polymer to a pair of nip rolls that flatten the monofilament to form a tape. A water quench cools and solidifies the tape, and the tape is wound onto a reel for supply to the inspection zone.

The reel onto which the tape is wound is transferred to a transport device for transporting the tape through the inspection zone. The transport device is analogous to a movie projector in that the tape is threaded through guide and tension rollers and through an illuminated inspection zone from a supply reel to a takeup reel.

The inspection zone includes a guide assembly for the tape for holding the tape in positional alignment with respect to a detector and light source. The guide assembly includes a first fixed guide slot for engaging one edge of the tape and through which the tape passes. A second guide slot opposite the first is movable and spring biased for accommodating small variations in the width of the tape as the tape is transported through the inspection zone.

In one embodiment, a source of ultraviolet light is provided adjacent the inspection zone for causing gels that may be present in a polyester polymer to fluoresce. The detector is a television camera that captures images of the gel fluorescence and creates a signal representative of the gel fluorescence. The signal is transmitted to an image analysis computer that counts the gels, sorts the gels into three preselected size ranges, calculates the total tape area occupied by the gels, and calculates the ratio of gel defect area to tape area.

In another embodiment, a source of polarized light is provided. Gels present in a polymer are made visible by rotation of the plane of polarized light, which creates images capturable by the camera that can be analyzed by a system similar to that discussed above with respect to fluorescent gels. Still other embodiments are discussed in the detailed description of the invention.

The method of the invention includes the steps of sampling molten polymer, transporting the polymer sample through an inspection zone for irradiating the polymer with electromagnetic radiation, detecting electromagnetic radiation that indicates the presence of defects in the polymer, and analyzing the detected radiation.

More specifically, a reactor output sample is converted into a tape for inspection. The step of detecting electromagnetic radiation includes capturing the images of gels created by the incidence of electromagnetic radiation on the polymer tape. The step of analyzing the detected radiation includes determining the total area of gels that may be present, determining the total area of tape inspected, and determining the ratio of gel area to tape area.

DETAILED DESCRIPTION OF THE PREFERRED EMBODIMENTS

Figure 1:
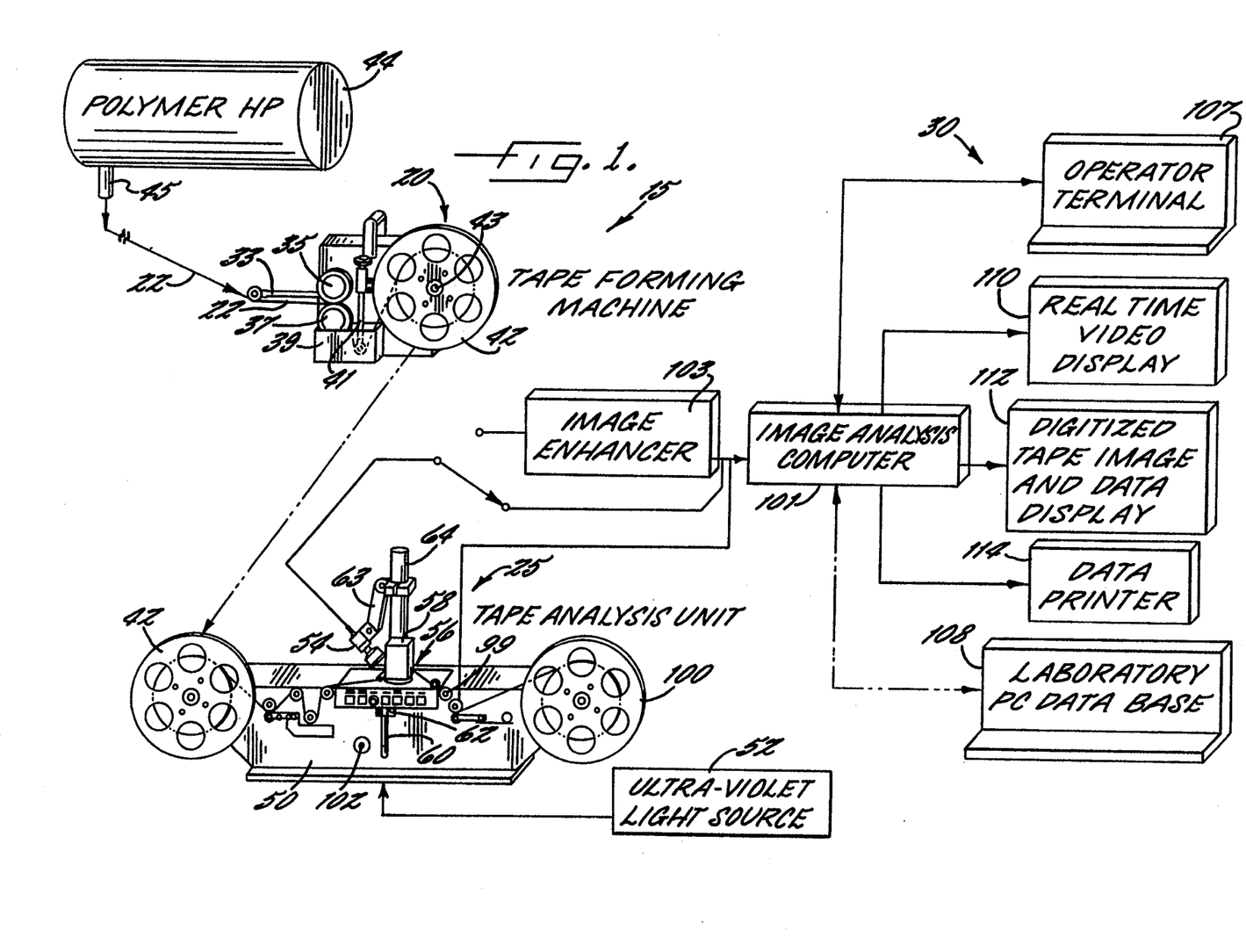
FIG. 1 is a perspective view of a specific embodiment of the tape forming and analysis apparatus of the invention claimed herein and a schematic representation of various electronic equipment.

FIG. 1 shows generally at 15 a perspective view of a preferred embodiment of an automated polymer defect test system of the invention claimed herein for the sampling of polymerization reactor output. In particular, FIG. 1 shows a system for analyzing defects in polyester polymer.

The polymer defect test system includes a tape forming machine 20 for converting a semi-molten polyester polymer monofilament 22 into a solid form having maximum surface area for optical inspection, a tape analysis unit 25 for inspecting the tape for defects, and associated electronics shown broadly at 30 for analysis and display of data.

Figure 2:
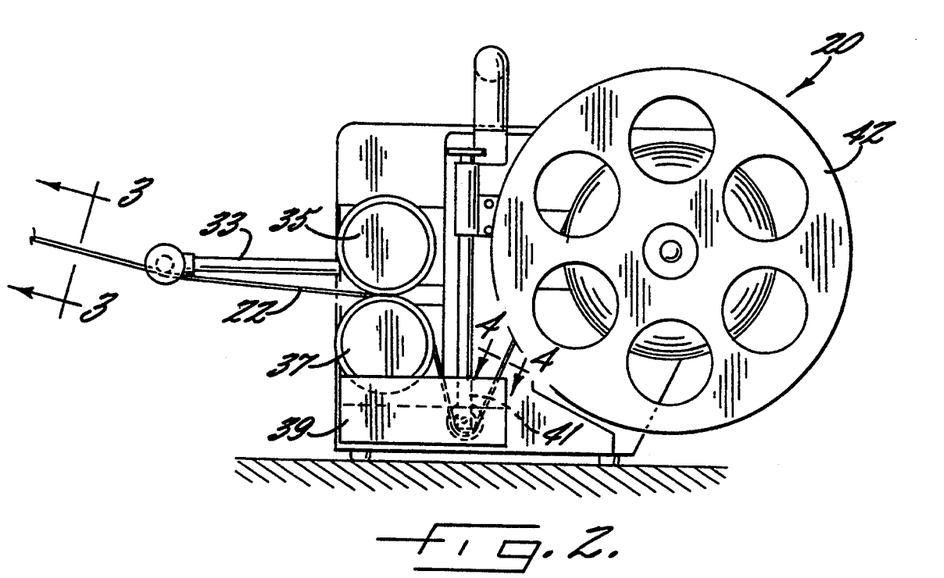
FIG. 2 is an elevation view of the tape forming portion of the apparatus illustrated in FIG. 1.
Figure 3:
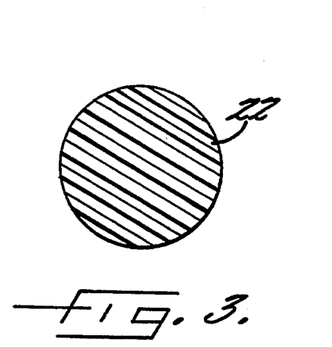
FIG. 3 is a representation of a cross section of a polymeric monofilament.
Figure 4:
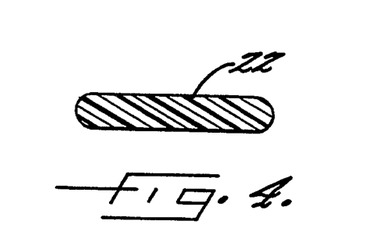
FIG. 4 is a representation of a cross section taken through a polyester monofilament that has been converted to a tape form.

Turning now to FIG. 2 for a more detailed discussion of the tape forming machine, tape forming machine 20 receives semi-molten monofilament polymer 22 by means of a guide assembly 33 that guides the monofilament to a nip located between nip rolls 35 and Polymer monofilament 22 is generally circular in cross-section as is represented in FIG. 3, which is taken along line 3—3 of FIG. 2. Nip rolls 35 and 37 convert polymer monofilament 22 into a flat tape, the cross-section of which is represented in FIG. 4, which is taken along line 4—4 of FIG. 2. The converted polymer tape then enters a water quench tank 39 via quench tank guide 41 where the tape is solidified and then wound onto takeup reel 42 of the tape forming machine 20, which takeup roll is mounted on a winder hub 43.

The tape forming machine 20 should preferably contain an air motor for operating the winder hub 43 that pulls the tape through the nip rolls and winds the tape onto the takeup reel. As will be readily understood by the skilled artisan, an air motor should be used for safety in hazardous environments. The tape produced by the tape forming machine is approximately 5.25 mm wide and about 0.3 mm thick. These dimensions provide a high surface area to volume ratio and optimize optical inspection for gels and other defects.

The semi-molten monofilament 22 is shown in FIG. 1 as being supplied from the high polymerization reactor ("Polymer HP") 44 of a polymerization unit through a bleed port 45. The bleed port 45 of the HP reactor 44 provides a means for obtaining a sample of the polymer in the reactor. The apparatus of the present invention has been adapted to receive a sample of semi-molten polymer monofilament through the bleed port 45, as explained below. The bleed port discharges to atmosphere and produces a thick monofilament at the rate of approximately 0.5 to 1.5 kg per hour and at a temperature of above about 500° F., which is convertible to about 400 meters of tape in about 20 minutes.

The tape forming machine 20 is operated to convert semi-molten polyester monofilament to tape as follows. The tape former 20 should be positioned near the polymer bleed 45. The semi-molten polymer stream 22 desirably is pulled down from the bleed 45 at an angle that does not cause the polymer to rub against the inside of the bleed. An air supply (not illustrated) is connected to the pneumatic driving motor for the tape forming machine. The water quench tank 39 is filled with water. The pneumatic motor is turned on to start the nip rolls 35 and 37 and the takeup reel 42. An operator cuts the bleed stream and inserts the bleed monofilament 22 into the nip rolls. Initially, the tape is pulled through the tape former 20 by hand and the quench tank guide 41 is lowered to position the tape under the surface of the water in the quench tank. The operator then wraps the tape around the takeup reel and cuts off the excess tape. Nip roll speed is set to provide a monofilament bleed tension adequate to prevent the monofilament from sagging to the floor or being pulled apart by too much tension. A nip roll cooling spray optionally may be maintained to optimize nip roll temperature.

It should be recognized that samples of semi-molten polymer monofilaments can be obtained from other locations than the bleed port 45 of HP reactor 44. Gels typically are produced in the polymerization reactors, and so samples should preferably be taken downstream of the HP reactor if not from the bleed port. For example, a polymer monofilament sample may be taken from a bleed stream of an extruder for melted polymer chips or from spin pack of a spinneret for the production of continuous filaments from molten polymer.

A spin pack is the complete assembly of filters and spinneret through which a polymer flows for spinning, which is a process for extruding the polymer through a plurality of small apertures in the spinneret for forming continuous filaments. In filament production, spin pack filters are used in part to remove gels that are formed in the reactor. Spin pack filters tend to break large gels down into smaller ones and tend to retain some of the gels. Nevertheless, sufficient gels may pass through the spin pack filter to be incorporated into filaments and to result in filament breakage in downstream processing. Sampling at the spin pack after polymer has flowed through the spin pack filter system has the advantage that the performance of spin pack filters in removing gels from the polymer can be evaluated.

Turning now to a discussion of the tape analysis unit illustrated generally at 25 in FIG. 1, takeup reel 42 is transferred to the tape analysis unit and becomes supply reel 42 for the tape analysis unit 25. The tape analysis unit 25 and the associated sensitive optical and electrical equipment to which takeup reel 42 is transferred should preferably be used in a clean environment in the absence of significant amounts of dust and heat.

Tape analysis unit 25 comprises a frame 50, attached to which is an ultraviolet light source 52 for illuminating the tape and creating fluorescent images therein, a camera 54 mounted on the opposite side of the tape from the illumination for capturing the fluorescent images (shown enlarged in FIG. 5), and an inspection zone 56 (shown enlarged in FIGS. 5, 6 and 7) for controlling the position of the tape with respect to the illumination and camera. Inspection zone 56 is shown in FIG. 1 with a protective metal cover 58 in place to protect the operator of the tape analysis unit from the effects of ultraviolet radiation when the system is operating. Camera 54 is mounted adjacent the inspection zone 56 on the side of the tape opposite the illumination to capture the images of defects in the polymer tape as the tape travels through the inspection zone. The camera 54 may be placed in locations other than on the opposite side of the tape from the illumination since gel fluorescence is emitted in all directions. For example, the camera may be placed on the same side of the tape as the illumination to capture images of gel fluorescence.

Ultraviolet light source 52 for the tape analysis unit 25 supplies ultraviolet light through a flexible light guide 60 to the inspection zone 56 for illumination of the polymer tape 22. Ultraviolet light can be provided from any suitable source. For example, a mercury vapor lamp that supplies a broad spectrum of electromagnetic radiation has been determined to be particularly useful in practicing the invention. The end of the light guide 60 adjacent the inspection stage is fitted with an interference filter 62 to attenuate light of wavelength other than about 300 to 400 nm to reduce the intensity of the non fluorescent images. The light source also is equipped with a safety shutter to close automatically when the cover 58 over the inspection stage is lifted.

Fluorescence of gels in polyester polymer typically occurs over a range of wavelengths of ultraviolet light of about 300 to 400 nm, although specific wavelengths may be selected for illumination with equivalent results. For example, the ultraviolet light source for inspection of polyester polymer gels can be provided by an ultraviolet laser or an electric arc source emitting light having a wavelength in the range of from about 300 to 400 nm. In the case of a laser source, filter 62 may be eliminated if desired since the light will be all of one wave length. A helium-cadmium laser emits ultraviolet light having a wavelength of 325 nm and is useful in the practice of the invention. Similarly, interference filters may be used that attenuate a portion of the ultraviolet spectrum from a broad spectrum source that causes fluorescence without eliminating all of the wavelengths that cause fluorescence. For example, an interference filter that attenuates light other than about 365 nm is useful in the practice of the invention.

It should be understood that a polarized visible light source can be used for inspection of polymer gels, without fluorescence, because gels and the stress concentrations associated with gels rotate the light in its plane of polarization. Accordingly, a polarized light source may be used for inspection of polyester polymer and other types of polymer than polyester. The tape may be stretched to create stress concentrations in the areas of gel defects that can be detected by rotation of the plane of polarized light.

Other light sources such as infrared and ordinary visible light can be used for inspection and determination of various information concerning the polymer tape. Visible light can be used for detection and analysis of black specks. An infrared source can be used to indicate the presence of certain terminal groups on the polymer chains. Any or all of these sources can be used in combination, with appropriate detectors and additional inspection stations, for analysis of a polymer sample tape, as will be explained further hereinbelow. However, for embodiments other than that using an ultraviolet source, the camera or other detector means for capturing electromagnetic radiation indicative of defects in the polymer tape typically will be located on the opposite side of the tape from the illumination. Most of these embodiments analyze changes in electromagnetic radiation occurring as a result of passing through the polymer tape, rather than analyzing electromagnetic radiation emitted from the tape.

Figure 5:
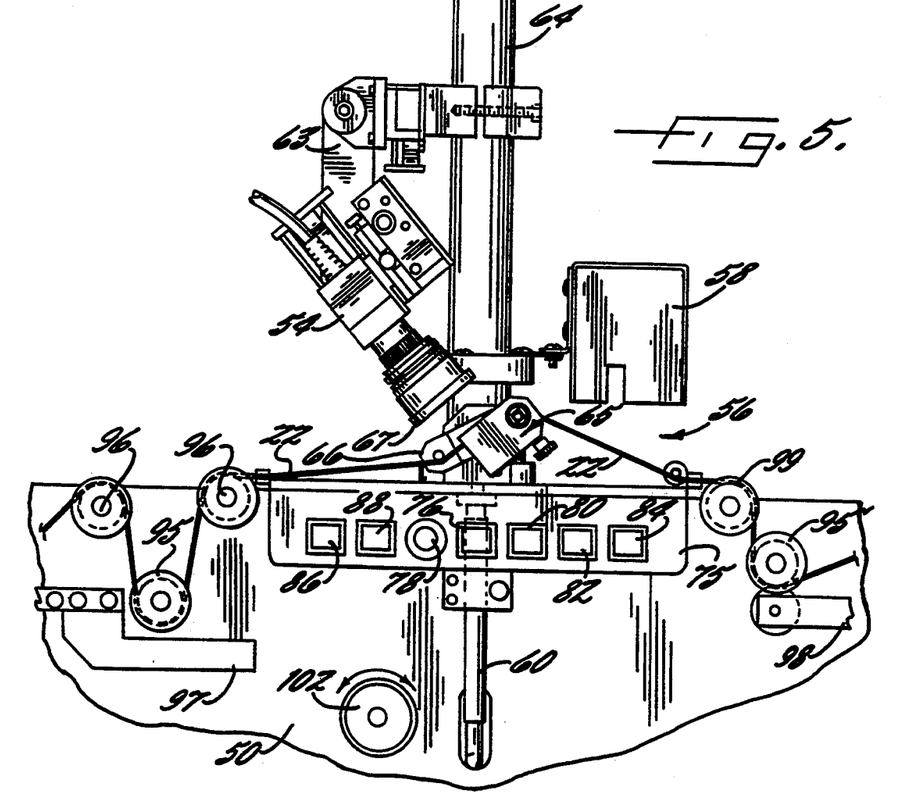
FIG. 5 is a partially broken away plan view of the tape analysis unit of FIG. 1.

Turning now to FIG. 5, a detector means, television camera 54, is mounted by means of an articulating linkage 63 to a support structure 64 mounted centrally on the frame of the tape analysis unit. The angle and height of the camera 54 can be adjusted by means of the articulating linkage 63 on the support structure to obtain the best possible images of defects in the polymer 22.

The skilled artisan will recognize that gel fluorescence images, rotated polarized light, and ordinary visible light may be captured by electronic or photographic camera means or a suitable sensor means, such as a photometer. An integrating photometer, which sums the total for the images captured, can be used where gross information on the total defect area is desired and it is not necessary to provide an analysis of the size range and distribution of defects such as gels or black specs. Filters may be provided to improve the image, as discussed hereinbelow. In the case of a relatively longer wavelength infrared source, the detector means could comprise a near infrared ("NIR") spectrophotometer for capturing gross information developed by the incidence of infrared radiation on the polymer sample. A spectrophotometer can determine the distribution of energy in a spectrum of luminous radiation, and so is useful in determining whether certain terminal groups are present on the polymer chains that affect the transmission of infrared light through the sample, and that indicate the polymer is not meeting specifications.

The camera 54 illustrated in FIG. 1 is equipped with a 50 mm F 1.4 lens assembly and 20 mm extension. Overall magnification is about 20 times. An interference filter 67 is mounted on the lens assembly. This filter passes the gel fluorescence wave lengths of about 500 to 700 nm and attenuates stray background light and the light used for illumination of the polymer tape. Filters 62 and 67 were selected so that the camera primarily sees gel fluorescence and the images of the sample tape and background disappear. The gels fluoresce over a range of wavelengths, so it is not necessary to pass the entire range to the camera. For example, an interference filter that attenuates light of other than about 650 nm provides equivalent results. The camera has a high sensitivity (greater than 0.1 lux) that is useful because of the relatively high attenuation of the interference filters.

Figure 6:
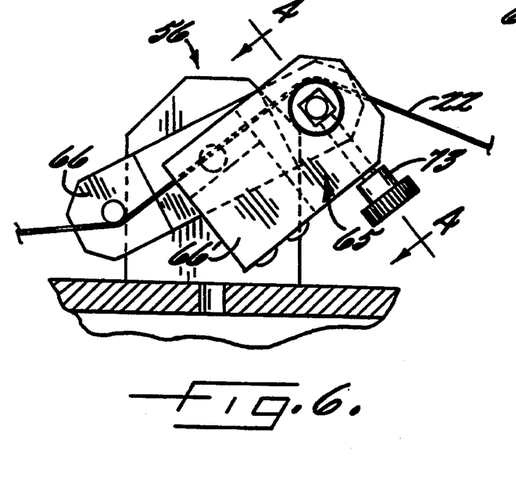
FIGS. 6 and 7 are enlarged representations of a side view and an end view, respectively, of portions of the apparatus illustrated in FIG. 5.
Figure 7:
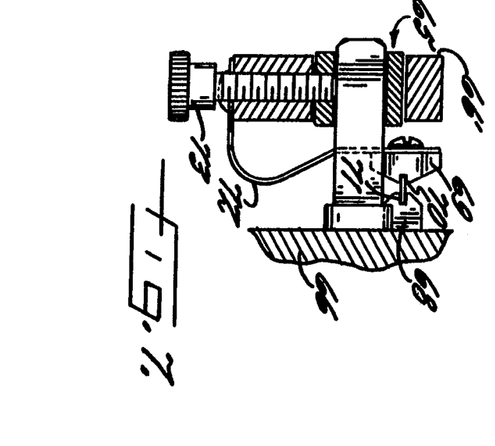

The function of the inspection zone 56 is to control the position of the sample tape with respect to the ultraviolet source 52 and the camera 54. Tape position is of particular importance since the camera lens system may have a shallow depth of field. Tape position is controlled by a guide assembly shown broadly at 65 (FIG. 6). The guide assembly comprises guide assembly mounting plates 66 and 66' and first and second guides 68 and 69, with first and second guide slots 70 and 71, respectively, for the edges of the tape (FIG. 7). The first guide 68 is fixed to the mounting plate 66 and the second guide 69 is biased against mounting plate 66' by a spring 72 to allow for slight changes in tape width.

The angle of the tape to the horizontal is adjustable. The tape is normally aligned to be perpendicular to the camera line of sight and at an incidence angle of about 70° to the illumination source. The camera is fixed at an angle of about 70° from the light source. FIGS. 6 and 7 show the guide assembly guiding the tape through the inspection zone and holding the tape in optical alignment with the camera. A micrometer adjusting mechanism 73 is illustrated in FIG. 6 mounted in guide plate 66' for moving the tape into position for analysis by the camera. The guide slots 70 and 71 cover the edges of the tape to control the tape position and to substantially preclude stray light at the tape edges from reaching the camera lens.

A control panel 75 is provided for controlling various functions and includes an on/off switch 76 for providing power to the unit, a speed control 78 for controlling the speed at which the tape travels through the inspection zone, a drive direction 80 for controlling the direction of travel of tape through the inspection zone, a jog switch 82 for moving the tape in the inspection zone, a run switch 84 for causing the tape to be transported continuously through the inspection zone, drive motor switch 86 for controlling the tape drive, and torque motor switch 88 for controlling the supply reel and takeup reel tensions through a pair of DC torque motors.

The tape analyzer unit 25 moves the polymer sample tape through the inspection zone 56 at accurately controlled speeds and tensions. Tape 22 is threaded from the supply reel 42 to the inspection zone 56 and the takeup reel 100 through a series of guide rollers 96 and is forwarded by a pair of tension rollers, which are stepper motor driven. These tension rollers are supply capstan roll 95 and takeup capstan roll 95'. A counter balance is shown at 97 on the supply side of the tape analysis unit to create a clutch-like effect in the event that the tape catches on the supply reel so that the reel will idle while the wheel continues to run. This operation avoids breaking tape and wear on the nip surfaces. A spring loaded nip mechanism 98 is located on the takeup side of the tape analysis unit. Takeup capstan 95' is operated at a slightly higher speed than supply capstan 95 to place the tape under tension as it travels through the inspection zone. The operation and cooperation among these elements is believed to be within the purview of the skilled artisan and so further discussion is not deemed necessary.

Tape analyzing unit 25 also includes an encoder wheel 99 that is driven by the sample tape. The encoder sends a pulse train signal to an image analysis computer, which is shown at 101 in FIG. 8, for calculation of the area of the polymer sample tape that has been inspected. The analyzer 25 also sends status signals to the image analysis computer 101 and accepts control signals from the computer. Finally, the tape analysis unit 25 also includes a manual tape positioner 102 so that a particularly interesting section of polymer tape can be manually centered on the inspection stage.

Figure 8:
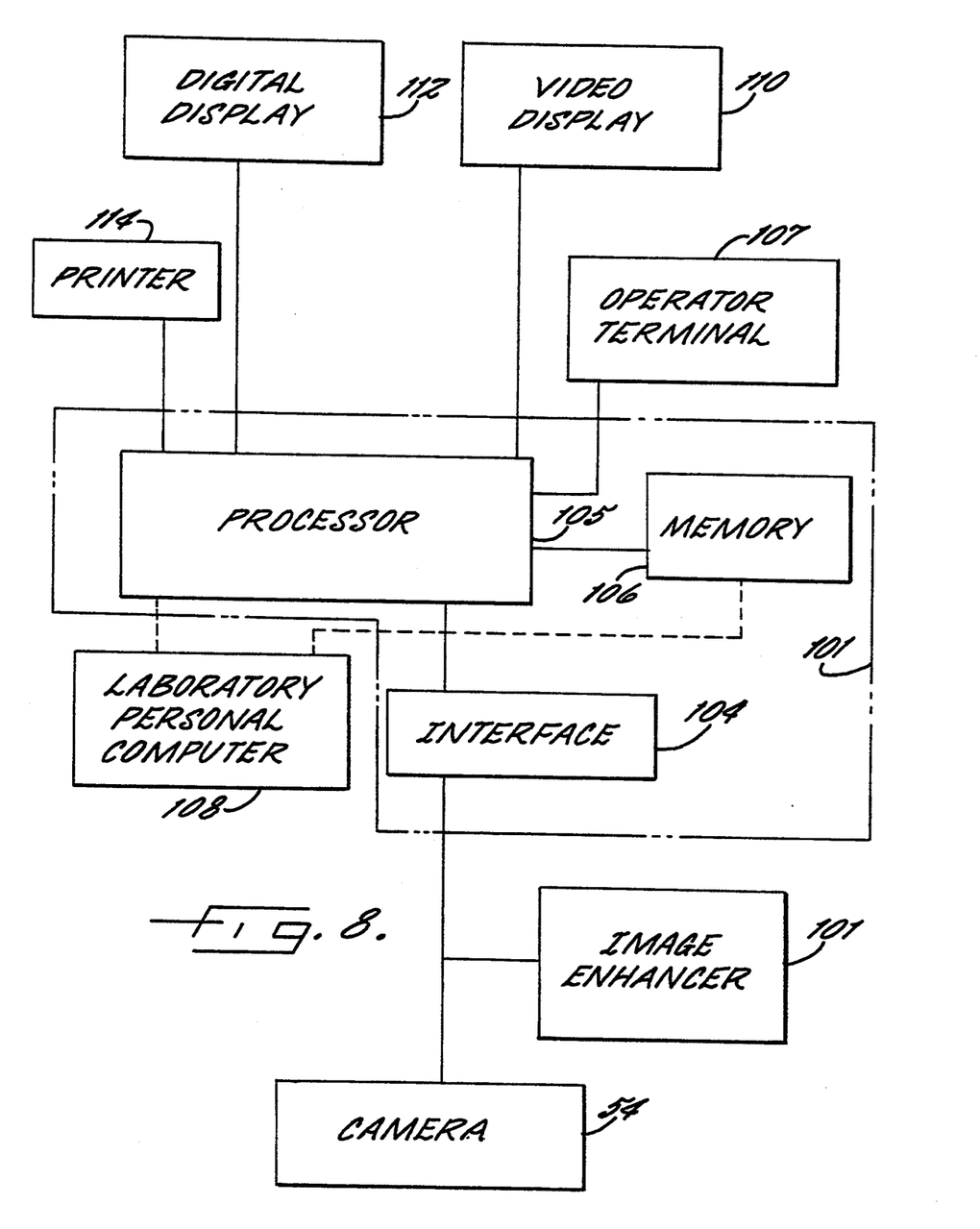
FIG. 8 is a schematic representation of the various optical and electronic equipment used in connection with the apparatus of FIG. 1.

FIG. 8 represents in schematic form an electronic diagram of various equipment that may be used in the present invention. The image analysis computer 101 functions to process the images or other information recorded from the camera or other detector. An image enhancer 103, such as an analog video enhancer module can be used to enhance gel images by shifting the video black level and compressing the gray scale. Such an analog video enhancer module is used primarily to make sample tapes from different sources look the same to the image analyzer. After enhancement, the camera signal is sent to the interface 104 of image analysis computer 101.

The image analysis computer 101 functions to process the images received from the camera or other detector. While only one camera has been illustrated, it should be understood that many commercially available image analysis computers can accept data from multiple detectors. The tape analysis unit can be designed to accommodate multiple inspection zones with different sources of electromagnetic radiation and appropriate detectors for each source. As shown in FIG. 8, the encoder wheel sends a signal to the computer interface 104 and processor 105 to retrieve the amount of sample tape inspected. The processor 105 measures the areas of the gels that are detected, sorts the gels into 3 size ranges selected by the operator at the start of the test, and computes the total number of gels, the total number of gels in each size range, and the total area of the gels. The processor then computes the sample defect ratio, which is defined as gel area divided by total inspected tape area. A memory function 106 is provided for storing data for comparison to various previous known conditions and for storing analysis parameters.

Figure 9A:
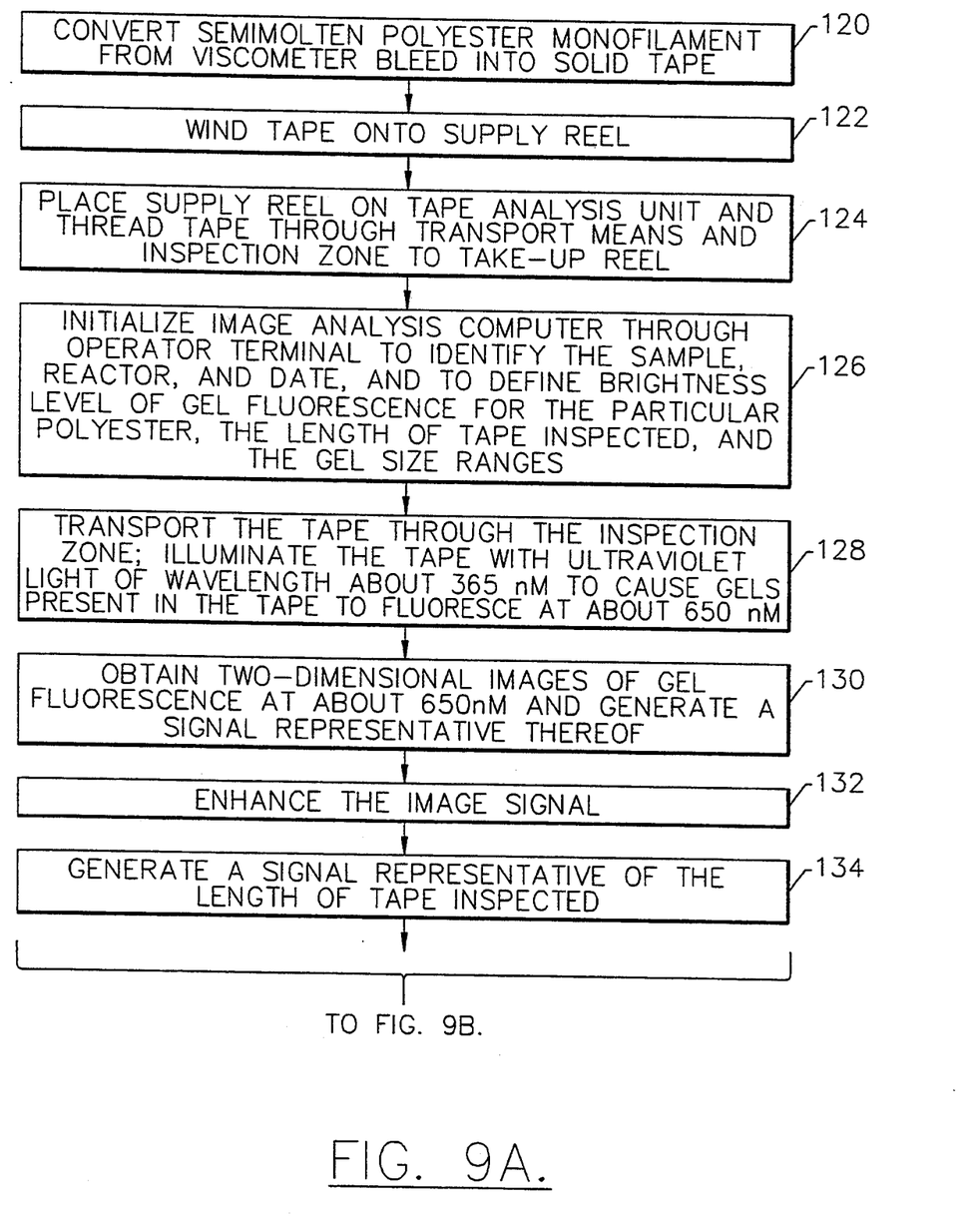
FIGS. 9A and 9B are a flow chart of the process steps for practice of the invention claimed herein.

An operator input terminal 107 is used to initialize the image analyzer computer 101 by entering sample identification data, gel size ranges, tape length to be analyzed, and to initiate the end of a test printout and/or to download data to a personal computer, as shown schematically at 108 and in the process flow diagram in FIG. 9A at 126.

The computer should be adjusted to detect and count the polymer gels by defining the brightness range and the size of the gels to be counted. Tapes from different reactors often have different appearances and quality limits. A library of gel counter setup information can be developed and stored in memory 106.

Image analysis computer 101 also supplies real time video images of the sample tape to a display 110 and digitized images of the tape with computed values of all test parameters to a display 112 as the analysis is in progress. Typical hard copy data printout on printer 114 could provide the following information:

Sample ID number:

Total number of contours processed, Size A:
Total number of contours processed, Size B:
Total number of contours processed, Size C:
Total area:
Defect Ratio:
Date Processed:
Time Processed:
Total tape area:

If desired, data from the image analysis computer 101 may be used as a basis for controlling a polymerization unit by adjusting process conditions or scheduling the unit for maintenance.

Figure 9B:
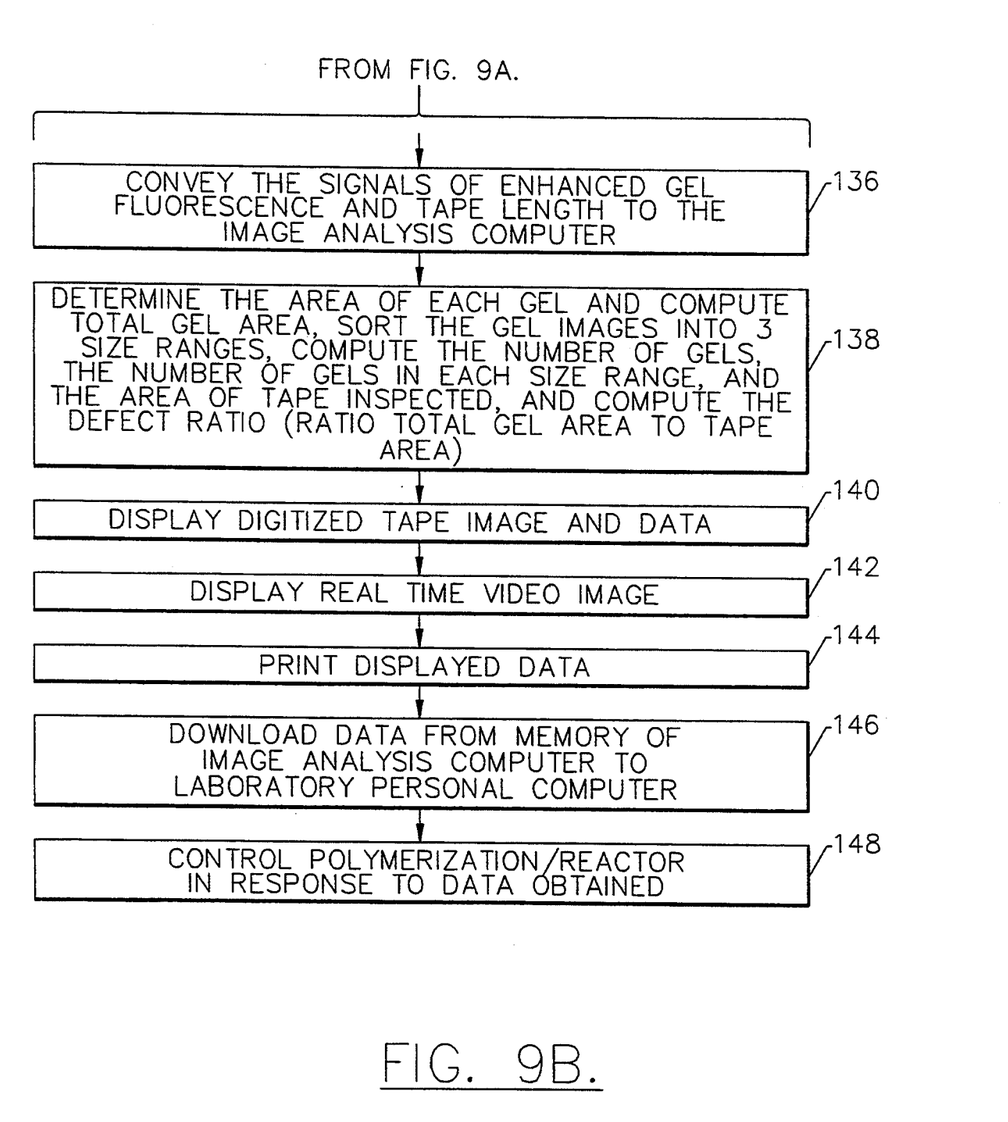

Operation of the automated polymer defect test system is illustrated by the flow diagram of FIGS. 9A and 9B. In the first steps 120, 122 and 124, the semi-molten polyester monofilament from the bleed is converted into a solid tape and is wound onto a supply reel for the tape analysis unit, as described hereinabove with respect to FIGS. 1 and 2. The operator then initializes the image analysis computer through the operator terminal, step 126, to identify the sample, the reactor, the date, to define brightness levels for gel fluorescence for the particular polyester, the length of the tape inspected and gel size ranges. Afterward, the operator loads the polymer sample tape into the tape analysis unit for transport through the inspection zone and illumination for inspection, step 128.

To illuminate the tape and operate the test system, the operator turns on the ultraviolet light source and loads the polymer sample tape reel onto the supply hub. The ultraviolet safety cover over the inspection stage can be lifted to thread the sample tape through the inspection zone. Lifting the safety cover automatically closes the safety shutter on the ultraviolet lamp to substantially preclude exposure of operators to ultraviolet radiation.

The sample tape is threaded through the inspection stage and onto the sample tape takeup reel. The ultraviolet safety cover on the inspection stage is closed to open the ultraviolet lamp safety shutter. Tape inspection speed is set according to the speed at which the image analysis computer can analyze the images. For the embodiment described herein, tape inspection speed typically is set at about 20 meters per hour.

The tape is started through the analyzer by closing the run switch on the control panel on the analyzer unit. The camera starts to capture images and generate signals representative thereof, step 130, when the run relay closes in the analyzer unit and the encoder pulse signal is received. It may be useful to enhance the signal, as described hereinabove with respect to FIG. 8, in accordance with step 132.

If operating the analyzer in the manual mode, then the test can be stopped by opening the run switch on the control panel. The encoder wheel supplies information on the length of tape inspected to the processor. In the automatic mode, the tape analyzer will stop when a preselected length of tape has been reached according to the signal generated by the encoder wheel, step 134.

The signals representing the images captured by the camera and the signal representing the length of tape inspected, as generated by the encoder wheel, are conveyed to the image analysis computer (step 136). The image analysis computer determines the area of each gel and computes the total gel area, sorts the gel images into three size ranges, computes the number of gels, the number of gels in each size range, and the area of tape inspected. The image analysis computer then computes the defect ratio, which is the ratio of the total gel area to the tape area, in accordance with the previous initialization of the computer, steps 138 and 126. Preferably, a hard copy data printout showing the total number of gels in each size range, the total area of the gels, and the defect ratio is provided in addition to digitized and real time tape images, in accordance with steps 140, 142 and 144. If desired, the data generated for analysis of a tape may be downloaded from the memory of the image analysis computer to a laboratory personal computer for statistical analysis and storage, in accordance with step 146. In accordance with step 148, reactor operating conditions can be manipulated in response to the data, or the reactor can be scheduled for maintenance, if necessary.

The invention has been described hereinabove with respect to particular preferred embodiments as illustrated in the drawings. However, these embodiments should be considered illustrative of and not in limitation of the invention claimed herein. The full scope of the invention should be judged in accordance with the appended claims and equivalents thereto.

What is claimed is:

1. Apparatus for detecting defects that may be present in a polymer, said apparatus comprising:
   (a) means for continually removing a sample of polymerization reactor output from a stream of molten polymer and converting said sample into a tape;
   (b) a polymer inspection zone for inspecting a preselected area of the tape for the presence of defects;
   (c) guide assembly means at said inspection zone, said guide assembly means having first and second guide slots for receiving first and second edge portions of the tape, respectively, for providing constant positional alignment of the tape within said inspection zone, said first guide slot being stationary and said second guide slot being movable to accommodate variations in the width of the tape as the tape travels through said inspection zone;
   (d) transport means for transporting the tape through said inspection zone;
   (e) a source of electromagnetic radiation positioned adjacent said inspection zone for irradiating the tape on one side thereof;
   (f) detector means positioned adjacent said inspection zone for detecting electromagnetic radiation indicative of defects present in the polymer, and generating an output signal representative thereof; and
   (g) analyzing means for receiving the output signal generated by said detector means and analyzing the signal to detect defects.

2. Apparatus of claim 1, wherein said source of electromagnetic radiation is selected from among the group consisting of sources of ultraviolet light, infrared light, polarized visible light, and visible light.

3. Apparatus of claim 1, further comprising a filter for limiting the wave length of electromagnetic radiation from said source that is incident on the polymer.

4. Apparatus of claim 1, further comprising a filter for limiting the background electromagnetic radiation reaching said detector means.

5. Apparatus of claim 1 for detecting the presence of gels in a polyester polymer, which gels fluoresce at about 500 to 700 nm when exposed to ultraviolet light of wavelength about 300 to 400 nm, and wherein said source of electromagnetic radiation is a source of ultraviolet radiation containing radiation of wavelength about 300 to 400 nm for causing the gels to fluoresce upon exposure to the source of radiation and said detector means is a camera for capturing the image of gels created by the fluorescence and generating an output signal representative thereof.

6. Apparatus of claim 5, wherein said source of ultraviolet radiation is selected from among the group consisting of a mercury vapor lamp, an ultraviolet laser, and an electric arc source.

7. Apparatus of claim 5, further comprising a first filter adjacent said source of ultraviolet light to limit the wavelengths of ultraviolet radiation incident on the polyester polymer to emphasize the effect of gel fluorescence and a second filter means adjacent said camera means to substantially reduce electromagnetic radiation captured by said camera means to that resulting from gel fluorescence.

8. Apparatus of claim 1 for detecting the presence of gels in a polymer, wherein said source of electromagnetic radiation is a source of polarized visible light and said detector means is a camera for capturing the images caused by the incidence of polarized visible light on the polymer and rotation of the plane of polarization of polarized light by stress concentrations associated with the gels.

9. Apparatus of claim 8, further comprising a cross-polarized filter adjacent said camera for substantially preventing polarized light from said source that has not been rotated in its plane of polarization by the stress concentrations from reaching said camera.

10. Apparatus of claim 1, wherein said source of electromagnetic radiation is a source of infrared light, said detector means is a spectrophotometer, and said analysis means comprises means for near infrared spectrographic analysis of the signal generated by said spectrophotometer.

11. Apparatus of claim 1, wherein said source of electromagnetic radiation is a source of visible light for creating an image of black specs in said polymer sample, and said detector is a camera for capturing the images.

12. Apparatus of claim 1, wherein said apparatus further comprises more than one source of electromagnetic radiation and corresponding additional detector means, and wherein said analyzing means receives the output signals of each of said detector means for analysis of defects.

13. Apparatus of claim 1, wherein said source of electromagnetic radiation includes a guide for conveying electromagnetic radiation to said polymer inspection zone.

14. Apparatus of claim 1, wherein said detector means is selected from the group consisting of a camera, an integrating photometer, and a spectrophotometer.

15. Apparatus of claim 14, wherein said camera is selected to have a sensitivity of at least about 0.1 lux.

16. Apparatus of claim 14, wherein said analyzing means includes a means for enhancing the image of the polymer defects captured by said photographic camera means by shifting the video black level and compressing the grey scale.

17. Apparatus of claim 1, wherein said analyzing means includes a processor for analyzing the signals and an operator terminal for initializing the processor with preselected parameters for analysis of defects.

18. Apparatus of claim 17, wherein said processor includes a memory and said apparatus further comprises a personal computer and associated data base for downloading of information from said memory of said processor.

19. Apparatus of claim 17 further comprising display means for displaying to a user of said apparatus an indication of the presence of defects that are detected in the polymer, said display means including a real time video display for displaying the image of the defects captured by said camera means, a digital display for displaying a digitized image of said defects and data, and a printer for printing the data developed by said processor.

20. Apparatus of claim 1, wherein the polymer sample is a polymer tape and said means for sampling of polymerization reactor output to obtain a polymer sample comprises means for converting a monofilament semi-molten polymer sample into a sample tape.

21. Apparatus of claim 20, wherein said conversion means for converting semi-molten polymer monofilament to tape comprises:

(a) a guide for guiding the semi-molten polymer monofilament;

(b) a pair of rolls forming a nip for receiving the monofilament from said guide and converting the monofilament to tape;

(c) water quench means for quenching the tape;

(d) a tape winder for winding the tape; and (e) a take-up reel mounted on said winder for receiving the tape.

22. Apparatus of claim 20, wherein said transport means includes a supply reel for supplying polymer tape to said inspection zone, a take-up reel for taking the tape up from said inspection zone, and a pair of tension rollers located between said supply roll and said take-up reel for controlling the tension applied to the tape as it travels through said inspection zone.

23. Automated apparatus for sampling of polymerization reactor output for detecting gels that may be present in a polymer, said apparatus comprising:

(a) a tape inspection zone for inspecting a preselected length of a polymer tape sample of the reactor output for the presence of gels;

(b) a supply reel for supplying the polymer tape to said inspection zone;

(c) a take-up reel for taking the tape up from said inspection zone;

(d) a pair of tension rollers located between said supply reel and said take-up reel for controlling the tension applied to the tape as it travels through said inspection zone;

(e) guide assembly means at said inspection zone, said guide assembly means having first and second guide slots for receiving first and second edge portions of the tape, respectively, for providing constant positional alignment of the tape within said inspection zone, said first guide slot being stationary and said second guide slot being movable to accommodate variations in the width of the tape as the tape travels through said inspection zone;

(f) an ultraviolet light source positioned adjacent said inspection zone for illuminating the tape with ultraviolet light so that gels present in said tape fluoresce;

(g) camera means positioned adjacent said inspection zone for inspecting the illuminated tape and generating an output signal representing two-dimensional images of gel fluorescence detected at said inspection zone, said camera means being optically aligned perpendicular to the tape;

(h) analyzing means for receiving the output signal generated by said camera means and for analyzing the signal to determine the total area of the gels detected that are of at least a predetermined size and emit fluorescence of at least a predetermined intensity, and determining the ratio of the total gel area of the total area of the tape inspected;

(i) a video monitor operatively connected to said analyzing means for displaying real time images for the gels; and (j) a digital monitor operatively connected to said analyzing means for displaying digitized images of the gels and numerical information from said analyzing means.

24. Automated apparatus for sampling of polymerization reactor output for detecting gels that may be present in polymer, said apparatus comprising:

(a) a tape inspection zone for inspecting a preselected length of a polymer tape sample of the reactor output for the presence of gels;

(b) a supply reel for supplying polymer tape to said inspection zone;

(c) a take-up reel for taking the tape up from said inspection zone;

(d) a pair of tension rollers located between said supply reel and said take-up reel for controlling the tension applied to the tape as it travels through said inspection zone;

(e) guide assembly means at said inspection zone, said guide assembly means having first and second guide slots for receiving first and second edge portions of the tape, respectively, for providing constant positional alignment of the tape within said inspection zone, said first guide slot being stationary and said second guide slot being movable to accommodate variations in the width of the tape as the tape travels through said inspection zone;

(f) a polarized light source positioned adjacent said inspection zone for illuminating the tape on a first side thereof with polarized light so that stress concentrations associated with gels present in the tape rotate the polarized light in the plane of polarization;

(g) camera means positioned adjacent said inspection zone for
inspecting the illuminated tape on a second side of the tape opposite the first side and generating an output
signal representing two-dimensional images of gels detected at said inspection zone, said camera means being optically aligned perpendicular to said guide assembly;

(h) a cross polarized filter adjacent said camera means so that said camera means captures the image of polarized light rotated in its plane of polarization while substantially eliminating polarized light that is not rotated;

(i) analyzing means for receiving the output signal generated by said camera means and for analyzing the signal to determine the total area of the gels detected that are of a predetermined size or larger, and determining the ratio of the total gel area to the total area of the tape inspected;

(j) a video monitor operatively connected to said analyzing means for displaying real time images of the gels; and (k) a digital monitor operatively connected to said analyzing means for displaying digitized images of the gels and numerical information from said analyzing means.

* * * * *